(12) United States Patent
Pescador et al.

(10) Patent No.: US 12,150,639 B2
(45) Date of Patent: Nov. 26, 2024

(54) TISSUE REMOVAL CONTAINMENT SYSTEMS

(71) Applicant: Applied Medical Resources Corporation, Rancho Santa Margarita, CA (US)

(72) Inventors: Cesar Pescador, Rancho Santa Margarita, CA (US); Joel Velasco, Rancho Santa Margarita, CA (US); Megan Garcia, Rancho Santa Margarita, CA (US); Deryk Perez, Rancho Santa Margarita, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 939 days.

(21) Appl. No.: 17/190,599

(22) Filed: Mar. 3, 2021

(65) Prior Publication Data

US 2021/0186639 A1   Jun. 24, 2021

Related U.S. Application Data

(63) Continuation of application No. PCT/US2019/052221, filed on Sep. 20, 2019.
(Continued)

(51) Int. Cl.
*A61B 17/02*   (2006.01)
*A61B 17/00*   (2006.01)
(Continued)

(52) U.S. Cl.
CPC .... *A61B 17/0293* (2013.01); *A61B 17/00234* (2013.01); *A61B 17/32002* (2013.01);
(Continued)

(58) Field of Classification Search
CPC ...... A61B 2560/04; A61B 2090/08021; A61B 2090/0801; A61B 2050/314;
(Continued)

(56) References Cited

U.S. PATENT DOCUMENTS 1,550,403 A   8/1925 Turkus
2,013,892 A   9/1935 Lucas
(Continued)

FOREIGN PATENT DOCUMENTS

DE        4405831 A1   8/1995
DE   102013217513 A1   3/2015
(Continued)

OTHER PUBLICATIONS

European Patent Office, The International Search Report and Written Opinion for International Application No. PCT/US2015/027274, entitled "Suture Clinch with Traction Enhanced," mailed Jul. 10, 2015, 14 pgs.
(Continued)

*Primary Examiner* — Jocelin C Tanner
(74) *Attorney, Agent, or Firm* — Patrick Ikehara

(57) ABSTRACT

The tissue removal containment system is provided that includes a tissue removal and/or containment bag arranged to be inserted through an opening into a confined space. The bag has a support or ring having a compressed, partially compressed and/or uncompressed state or position. The bag can also include an enclosure or film defining the enclosure connected to the support with the enclosure having a confined state and a deployed or unconfined state.

19 Claims, 9 Drawing Sheets

Related U.S. Application Data

(60) Provisional application No. 62/734,093, filed on Sep. 20, 2018.

(51) Int. Cl.
- *A61B 17/32* (2006.01)
- *A61B 17/34* (2006.01)
- *A61B 17/42* (2006.01)
- *A61B 50/30* (2016.01)
- *A61B 90/00* (2016.01)
- *A61B 90/40* (2016.01)

(52) U.S. Cl.
CPC .......... *A61B 17/3423* (2013.01); *A61B 17/42* (2013.01); *A61B 50/30* (2016.02); *A61B 90/40* (2016.02); *A61B 2017/00287* (2013.01); *A61B 2017/0225* (2013.01); *A61B 2017/320024* (2013.01); *A61B 2017/3433* (2013.01); *A61B 2017/3466* (2013.01); *A61B 2017/347* (2013.01); *A61B 2017/4216* (2013.01); *A61B 2050/314* (2016.02); *A61B 2090/08021* (2016.02); *A61B 2560/04* (2013.01)

(58) Field of Classification Search
CPC ...... A61B 2017/4216; A61B 2017/347; A61B 2017/3466; A61B 2017/3433; A61B 2017/320024; A61B 2017/0225; A61B 2017/00287; A61B 90/40; A61B 50/30; A61B 17/42; A61B 17/3423; A61B 17/32002; A61B 17/0293; A61B 17/00234; A61B 10/0291; A61B 10/0096
See application file for complete search history.

(56) References Cited

U.S. PATENT DOCUMENTS

| | | | |
|---|---|---|---|
| 2,812,758 | A | 11/1957 | Blumenschein |
| 3,244,169 | A | 4/1966 | Baxter |
| 3,762,417 | A | 10/1973 | Textor |
| 3,807,393 | A | 4/1974 | McDonald |
| 4,120,301 | A | 10/1978 | Lovick |
| 4,553,537 | A | 11/1985 | Rosenberg |
| 4,573,452 | A | 3/1986 | Greenberg |
| 5,037,379 | A * | 8/1991 | Clayman .......... A61B 17/00234 128/850 |
| 5,143,082 | A | 9/1992 | Kindberg et al. |
| 5,213,114 | A | 5/1993 | Bailey, Jr. |
| 5,215,101 | A | 6/1993 | Jacobs et al. |
| 5,215,521 | A | 6/1993 | Cochran et al. |
| 5,224,930 | A | 7/1993 | Spaeth et al. |
| 5,231,974 | A | 8/1993 | Giglio et al. |
| 5,308,327 | A | 5/1994 | Heaven et al. |
| 5,312,416 | A | 5/1994 | Spaeth et al. |
| 5,320,627 | A | 6/1994 | Sorensen et al. |
| 5,330,483 | A | 7/1994 | Heaven et al. |
| 5,337,754 | A | 8/1994 | Heaven et al. |
| 5,354,303 | A | 10/1994 | Spaeth et al. |
| 5,368,545 | A | 11/1994 | Schaller et al. |
| 5,465,731 | A | 11/1995 | Bell et al. |
| 5,486,183 | A | 1/1996 | Middleman et al. |
| RE35,164 | E | 3/1996 | Kindberg et al. |
| 5,520,610 | A | 5/1996 | Giglio et al. |
| 5,611,803 | A | 3/1997 | Heaven et al. |
| 5,618,296 | A | 4/1997 | Sorenson et al. |
| 5,636,639 | A | 6/1997 | Turturro et al. |
| 5,647,372 | A | 7/1997 | Tovey et al. |
| 5,649,550 | A | 7/1997 | Crook |
| 5,669,927 | A | 9/1997 | Boebel et al. |
| 5,769,794 | A | 6/1998 | Conlan et al. |
| 5,785,677 | A | 7/1998 | Auweiler |
| 5,788,709 | A | 8/1998 | Riek et al. |
| 5,810,721 | A | 9/1998 | Mueller et al. |
| 5,836,936 | A | 11/1998 | Cuschieri |
| 5,895,392 | A | 4/1999 | Riek et al. |
| 5,957,884 | A | 9/1999 | Hooven |
| 5,971,995 | A | 10/1999 | Rousseau |
| 6,036,681 | A | 3/2000 | Hooven |
| 6,039,748 | A | 3/2000 | Savage et al. |
| 6,045,566 | A | 4/2000 | Pagedas |
| 6,048,309 | A | 4/2000 | Flom et al. |
| 6,059,793 | A | 5/2000 | Pagedas |
| 6,142,935 | A | 11/2000 | Flom et al. |
| 6,162,172 | A | 12/2000 | Cosgrove et al. |
| 6,206,889 | B1 | 3/2001 | Bennardo |
| 6,228,095 | B1 | 5/2001 | Dennis |
| 6,254,534 | B1 | 7/2001 | Butler et al. |
| 6,258,102 | B1 | 7/2001 | Pagedas |
| 6,270,505 | B1 | 8/2001 | Yoshida et al. |
| 6,350,267 | B1 | 2/2002 | Stefanchik |
| 6,382,211 | B1 | 5/2002 | Crook |
| 6,387,102 | B2 | 5/2002 | Pagedas |
| 6,406,440 | B1 | 6/2002 | Stefanchik |
| 6,569,105 | B1 | 5/2003 | Kortenbach et al. |
| 6,685,628 | B2 | 2/2004 | Vu |
| 6,814,700 | B1 | 11/2004 | Mueller et al. |
| 6,958,037 | B2 | 10/2005 | Ewers et al. |
| 7,041,055 | B2 | 5/2006 | Young et al. |
| 7,238,154 | B2 | 7/2007 | Ewers et al. |
| 7,297,106 | B2 | 11/2007 | Yamada et al. |
| 7,377,898 | B2 | 5/2008 | Ewers et al. |
| 7,491,168 | B2 | 2/2009 | Raymond et al. |
| 7,537,564 | B2 | 5/2009 | Bonadio et al. |
| 7,547,310 | B2 | 6/2009 | Whitfield |
| 7,670,346 | B2 | 3/2010 | Whitfield |
| 7,758,500 | B2 | 7/2010 | Boyd et al. |
| 7,758,501 | B2 | 7/2010 | Frasier et al. |
| 7,762,969 | B2 | 7/2010 | Gellman et al. |
| 7,896,877 | B2 | 3/2011 | Hall et al. |
| 7,955,292 | B2 | 6/2011 | Leroy et al. |
| 7,981,130 | B2 | 7/2011 | Seeh |
| 7,998,068 | B2 | 8/2011 | Bonadio et al. |
| 8,016,771 | B2 | 9/2011 | Orban, III |
| 8,016,839 | B2 | 9/2011 | Wilk |
| 8,038,611 | B2 | 10/2011 | Raymond et al. |
| 8,075,567 | B2 | 12/2011 | Taylor et al. |
| 8,100,928 | B2 | 1/2012 | Nohilly et al. |
| 8,114,119 | B2 | 2/2012 | Spivey et al. |
| 8,152,820 | B2 | 4/2012 | Mohamed et al. |
| 8,157,834 | B2 | 4/2012 | Conlon |
| 8,337,510 | B2 | 12/2012 | Rieber et al. |
| 8,366,754 | B2 | 2/2013 | Teague et al. |
| 8,409,112 | B2 | 4/2013 | Wynne et al. |
| 8,409,216 | B2 | 4/2013 | Parihar et al. |
| 8,414,596 | B2 | 4/2013 | Parihar et al. |
| 8,425,533 | B2 | 4/2013 | Parihar et al. |
| 8,444,655 | B2 | 5/2013 | Parihar et al. |
| 8,517,935 | B2 | 8/2013 | Marchek et al. |
| 8,579,914 | B2 | 11/2013 | Menn et al. |
| 8,597,180 | B2 | 12/2013 | Copeland et al. |
| 8,622,897 | B2 | 1/2014 | Raymond et al. |
| 8,721,538 | B2 | 5/2014 | Bucholz |
| 8,721,658 | B2 | 5/2014 | Kahle et al. |
| 8,734,336 | B2 | 5/2014 | Bonadio et al. |
| 8,777,849 | B2 | 7/2014 | Haig et al. |
| 8,821,377 | B2 | 9/2014 | Collins |
| 8,857,440 | B2 | 10/2014 | Gundlapalli et al. |
| 8,864,658 | B2 | 10/2014 | Wilkins et al. |
| 8,920,431 | B2 | 12/2014 | Shibley et al. |
| 8,956,286 | B2 | 2/2015 | Shibley et al. |
| 8,961,408 | B2 | 2/2015 | Wilkins et al. |
| 8,961,409 | B2 | 2/2015 | O'Prey et al. |
| 9,039,610 | B2 | 5/2015 | Wilkins et al. |
| 9,044,210 | B1 | 6/2015 | Hoyte et al. |
| 9,168,031 | B2 | 10/2015 | Copeland et al. |
| 9,265,492 | B2 | 2/2016 | Shibley et al. |
| 9,877,740 | B2 | 1/2018 | Sullivan et al. |
| 10,188,374 | B2 | 1/2019 | Shibley et al. |
| 2004/0097960 | A1 | 5/2004 | Terachi et al. |
| 2004/0158261 | A1 | 8/2004 | Vu |
| 2005/0171405 | A1 | 8/2005 | Rowland et al. |
| 2005/0267492 | A1 | 12/2005 | Poncet et al. |
| 2006/0200169 | A1 | 9/2006 | Sniffin |

(56) References Cited

U.S. PATENT DOCUMENTS

| | | |
|---|---|---|
| 2006/0200170 A1 | 9/2006 | Aranyi |
| 2007/0051375 A1 | 3/2007 | Milliman |
| 2007/0135780 A1 | 6/2007 | Pagedas |
| 2007/0161866 A1 | 7/2007 | Fowler, Jr. et al. |
| 2007/0161867 A1 | 7/2007 | Fowler, Jr. et al. |
| 2009/0138024 A1 | 5/2009 | Ichihara et al. |
| 2009/0264710 A1 | 10/2009 | Chana et al. |
| 2010/0219091 A1 | 9/2010 | Turner |
| 2011/0054260 A1 | 3/2011 | Albrecht et al. |
| 2011/0184311 A1 | 7/2011 | Parihar et al. |
| 2011/0184435 A1 | 7/2011 | Parihar et al. |
| 2011/0190779 A1 | 8/2011 | Gell et al. |
| 2011/0319719 A1 | 12/2011 | O'Prey et al. |
| 2012/0078264 A1 | 3/2012 | Taylor et al. |
| 2012/0083795 A1 | 4/2012 | Fleming et al. |
| 2012/0109144 A1 | 5/2012 | Chin et al. |
| 2012/0157777 A1 | 6/2012 | Okoniewski |
| 2012/0238823 A1 | 9/2012 | Hagerty et al. |
| 2012/0316572 A1 | 12/2012 | Rosenblatt et al. |
| 2013/0103042 A1 | 4/2013 | Davis |
| 2013/0103043 A1 | 4/2013 | Cabrera |
| 2013/0131457 A1 | 5/2013 | Seckin |
| 2013/0138115 A1 | 5/2013 | Seckin |
| 2013/0184536 A1 | 7/2013 | Shibley et al. |
| 2013/0284186 A1 | 10/2013 | Touati |
| 2014/0052018 A1 | 2/2014 | Hawkins |
| 2014/0058210 A1 | 2/2014 | Raymond et al. |
| 2014/0058403 A1 | 2/2014 | Menn et al. |
| 2014/0135788 A1 | 5/2014 | Collins |
| 2014/0235952 A1 | 8/2014 | Haig et al. |
| 2014/0236110 A1 | 8/2014 | Taylor et al. |
| 2014/0236167 A1 | 8/2014 | Shibley et al. |
| 2014/0296649 A1 | 10/2014 | Fehling et al. |
| 2014/0316210 A1 | 10/2014 | Koehler et al. |
| 2014/0330285 A1 | 11/2014 | Rosenblatt et al. |
| 2015/0005584 A1 | 1/2015 | Wilkins et al. |
| 2015/0018625 A1 | 1/2015 | Miraki et al. |
| 2015/0094541 A1 | 4/2015 | Wilkins et al. |
| 2015/0119647 A1 | 4/2015 | Vaillancourt et al. |
| 2015/0297254 A1* | 10/2015 | Sullivan ............... A61B 17/221 606/114 |
| 2016/0066934 A1 | 3/2016 | Antonelli et al. |
| 2016/0100857 A1 | 4/2016 | Wachli et al. |
| 2016/0183932 A1 | 6/2016 | Shibley et al. |
| 2016/0199051 A1 | 7/2016 | Shibley et al. |
| 2016/0242751 A1 | 8/2016 | Bonadio et al. |
| 2017/0215904 A1 | 8/2017 | Wassef et al. |
| 2017/0252026 A1 | 9/2017 | Gupta et al. |
| 2019/0090863 A1 | 3/2019 | Shibley et al. |

FOREIGN PATENT DOCUMENTS

| | | |
|---|---|---|
| EP | 1 312 318 A1 | 5/2003 |
| EP | 1 935 356 A1 | 6/2008 |
| EP | 2 138 113 A2 | 12/2009 |
| EP | 2 359 758 A2 | 8/2011 |
| EP | 2 668 907 A2 | 12/2013 |
| WO | WO 00/32116 A1 | 6/2000 |
| WO | WO-03013982 A1 * | 2/2003 ........... B65D 21/086 |
| WO | WO 03/061480 A1 | 7/2003 |
| WO | WO 03/071926 A2 | 9/2003 |
| WO | WO 2004/075730 A2 | 9/2004 |
| WO | WO 2008/083222 A2 | 7/2008 |
| WO | WO 2011/143410 A1 | 11/2011 |
| WO | WO 2013/093030 A2 | 6/2013 |
| WO | WO 2013/150391 A1 | 10/2013 |
| WO | WO 2015/164591 A1 | 10/2015 |
| WO | WO 2017/189442 A1 | 11/2017 |
| WO | WO 2018/161769 A1 | 9/2018 |
| WO | WO 2018/161770 A1 | 9/2018 |

OTHER PUBLICATIONS

European Patent Office, The International Search Report and Written Opinion for International Application No. PCT/US2015/056978, entitled "Systems and Methods for Tissue Removal," mailed Jan. 15, 2016, 13 pgs.

European Patent Office, The International Search Report and Written Opinion for International Application No. PCT/US2015/045705, entitled "Systems and Methods for Tissue Containment and Retrieval," mailed Apr. 18, 2016, 18 pgs.

European Patent Office, The International Search Report and Written Opinion for International Application No. PCT/US2016/029154, entitled "Systems and Methods for Tissue Removal," mailed Aug. 23, 2016, 17 pgs.

The International Bureau of WIPO, International Preliminary Report on Patentability for International Application No. PCT/US2015/027274, entitled "Systems and Methods for Tissue Removal," mailed Nov. 3, 2016, 9 pgs.

The International Bureau of WIPO, International Preliminary Report on Patentability for International Application No. PCT/US2015/045705, entitled "Systems and Methods for Tissue Containment and Retrieval," mailed Mar. 2, 2017, 10 pgs.

European Patent Office, Invitation to Pay Additional Fees for International Application No. PCT/US2017/014402, titled "Systems and Methods for Tissue Removal", mailed Apr. 6, 2017, 10pgs.

The International Bureau of WIPO, International Preliminary Report on Patentability for International Application No. PCT/US2015/056978, entitled "Systems and Methods for Tissue Removal," mailed May 26, 2017, 10 pgs.

European Patent Office, The International Search Report and Written Opinion for International Application No. PCT/US2017/014402, entitled "Systems and Methods for Tissue Removal," mailed Jun. 6, 2017, 20 pgs.

The International Bureau of WIPO, International Preliminary Report on Patentability for International Application No. PCT/US2016/029154, entitled "Systems and Methods for Tissue Removal," mailed Nov. 2, 2017, 11pgs.

The International Bureau of WIPO, International Preliminary Report on Patentability for International Application No. PCT/US2017/014402, entitled "Systems and Methods for Tissue Removal," mailed Aug. 2, 2018, 11pgs.

The International Bureau of WIPO, International Preliminary Report on Patentability for International Application No. PCT/US2019/052221, entitled "Tissue Removal Containment Systems," mailed Sep. 20, 2018, 11pgs.

European Patent Office, Invitation to Pay Additional Fees for International Application No. PCT/US2019/052221, titled "Tissue Removal Containment Systems," mailed Jan. 3, 2020, 14pgs.

European Patent Office, The International Search Report and Written Opinion for International Application No. PCT/US2019/052221, entitled "Tissue Removal Containment Systems," mailed Mar. 4, 2020, 22 pgs.

* cited by examiner

TISSUE REMOVAL CONTAINMENT SYSTEMS

CROSS-REFERENCE TO RELATED APPLICATIONS

This application is a continuation of International Application No. PCT/US2019/052221, filed on Sep. 20, 2019, which claims priority to and benefit of U.S. Provisional Application No. 62/734,093, filed on Sep. 20, 2018, the entire disclosures of which are hereby incorporated by reference as if set in full herein.

BACKGROUND

The present application is generally directed to tissue removal systems and methods and more particularly to systems and methods for the containment of tissue prior to and/or during morcellation procedures.

Specimens retrieved during certain surgical procedures require specimen containment and extraction. In one such exemplary surgical operation, single site gynecological procedures such as laparoscopic hysterectomies have limited visualization of the surgical space and surroundings, especially in large uteri cases, as the volume of the specimen can occupy a vast majority of the surgical space. As such, full visualization of the specimen from the access site is not achieved in such cases, requiring the laparoscope to be constantly manipulated proximal to the access site to allow for visualization. Also, due to the limited surgical space, repositioning or generally moving the specimen within the confined surgical space is also difficult. Additionally, in a laparoscopic hysterectomy, a uterus is dissected, mobilized and collected. The uterus is removed through a trocar or an incision, ranging in size from 2.5 cm to 4 cm, thus adding to the difficulty in collecting and containing the specimen. Methods and systems of collecting and containing such a specimen in this or other procedures have shortcomings and improvements of such methods and systems desired.

SUMMARY

In accordance with various embodiments, a containment system is provided. The containment system comprises a containment bag arranged to be inserted through a body opening and in various embodiments is arranged to accommodate a range of specimen sizes that is larger than a trocar incision size. The containment bag is configured to mitigate the potential spread or displacement of unwanted tissue during morcellation or other similar surgical procedures.

In accordance with various embodiments, a tissue containment bag comprises a support or ring having an inner periphery delimiting an open end, the ring being deformable from an initial uncompressed state in which the open end delimited by the ring is unobstructed to a compressed state in which the open end delimited by the ring is partially obstructed. The bag further comprises a film connected to the ring to form an enclosure having an interior and a closed end, the interior of the enclosure being accessible through the open end delimited by the ring. The film and the interior of the enclosure is extendable to a deployed state in which a distalmost end of the film extends away from the ring from a confined state in which the film including the distalmost end is confined to a position adjacent to ring. The bag in various embodiments further comprises a strap connected to the ring with the strap having a fastened state in which the strap in the fastened state secures the ring in the compressed state and, simultaneously, the film in the confined state. In various embodiments, the strap has an unfastened state in which the strap simultaneously releases the ring from its compressed state and the film from its confined state. In various embodiments, the strap has a fastener attachment releasably connected the strap to itself. In various embodiments, the bag has a tab connected to the ring at a position opposite of a strap. In various embodiments, the bag has a first tab connected to a position on the ring to the position of the strap and a second tab connected to at a position on the ring between the first tab and a strap.

In accordance with various other embodiments, a tissue containment system is provided. The system comprises a tissue containment bag and a surgical tool or instrument arranged to insert or facilitate insertion of the tissue containment bag into a patient's body cavity, convert a ring of the tissue containment bag from a compressed state to an uncompressed state and a film of the tissue containment bag from a confined state to a deployed state, and/or convert the ring of the tissue containment bag from an uncompressed state to a partially compressed state.

In accordance with various embodiments, a method of preparing a tissue containment bag for deployment comprises providing a tissue containment bag comprising a ring and a film connected to the ring with the film defining an enclosure, placing the ring in a compressed state, placing the film in a confined state, and/or securing the ring in its compressed state and the film in its confined state.

In accordance with various embodiments, a method of deploying a tissue containment bag is provided. The method comprises providing a tissue containment bag comprising a ring or support, a film connected to the ring and a strap connected to the ring and the film with the film defining an enclosure, placing the ring in a compressed state and the film in a confined state, wrapping the strap connected to the ring around portions of the ring and portions of the film, fastening the strap to itself, inserting the tissue containment bag into a confined space with the ring in a compressed state and the film in a confined state, the entire film being gathered and placed adjacent to the ring and secured within an outer periphery of the ring with the ring defining a narrowed opening and having a hourglass shape, and/or unfastening the strap from itself releasing the film from its confined state and the ring from its compressed state.

In accordance with various embodiments, a method of removing a specimen is provided. The method comprises providing a tissue containment bag comprising a ring or support and a film connected to the ring with the film defining an enclosure, placing the ring in a compressed state and the film in a confined state, securing the ring in its compressed state and the film in its confined state, inserting the tissue containment bag into a patient's cavity with the ring in a compressed state and the film in a confined state, releasing the film from its confined state to its deployed state and the ring from its compressed state to its uncompressed state, placing a specimen through an opening defined by the ring in its uncompressed state and into the enclosure defined by the film in its deployed state, partially closing the opening defined by the ring to secure the ring in a partially compressed state while the film remains in its deployed state, removing the ring in its partially compressed state out of the patient's cavity with the film remaining within the patient's cavity, releasing the ring from its partially compressed state to move to its uncompressed state, and/or removing the specimen from the enclosure and out through the opening of the ring. The above methods in various embodiments can also comprise of closing a portion of the enclosure between the ring or support and the film and/or closing a portion of the enclosure between the ring or support and the film by pulling a cinch way from the film, the cinch being connected to the film and positioned below the ring.

In accordance with various embodiments, a tissue containment bag is provided. The bag comprises a support or ring connected to an enclosure or a film defining an enclosure and at least one of a strap, a tab, a cord and/or a cinch or any combination thereof.

Many of the attendant features of the present inventions will be more readily appreciated as the same becomes better understood by reference to the foregoing and following description and considered in connection with the accompanying drawings.

BRIEF DESCRIPTION OF THE DRAWINGS

The present inventions may be better understood taken in connection with the accompanying drawings in which the reference numerals designate like parts throughout the figures thereof.

DETAILED DESCRIPTION

Figure 1:
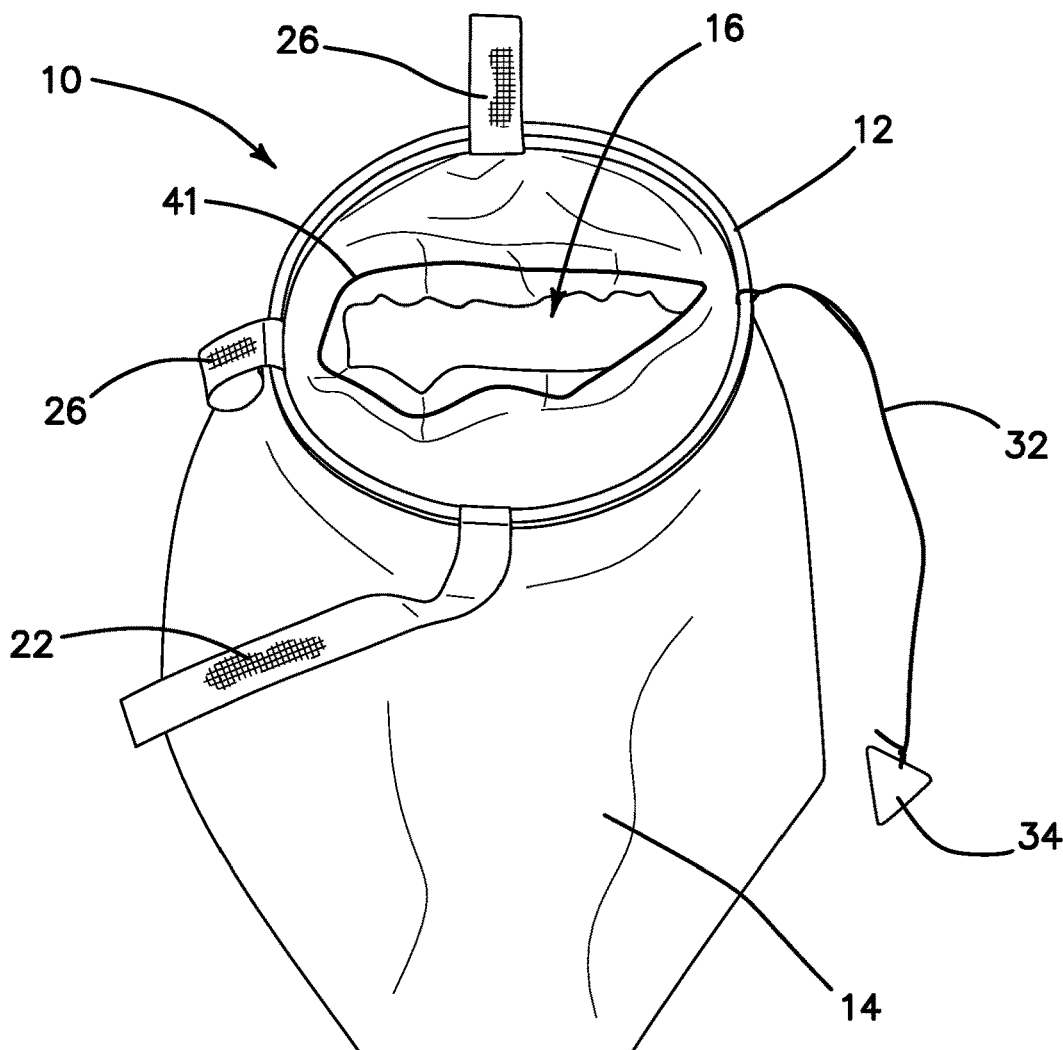
FIG. 1 is a top perspective view of a containment bag in accordance with various embodiments of the present invention.
Figure 2:
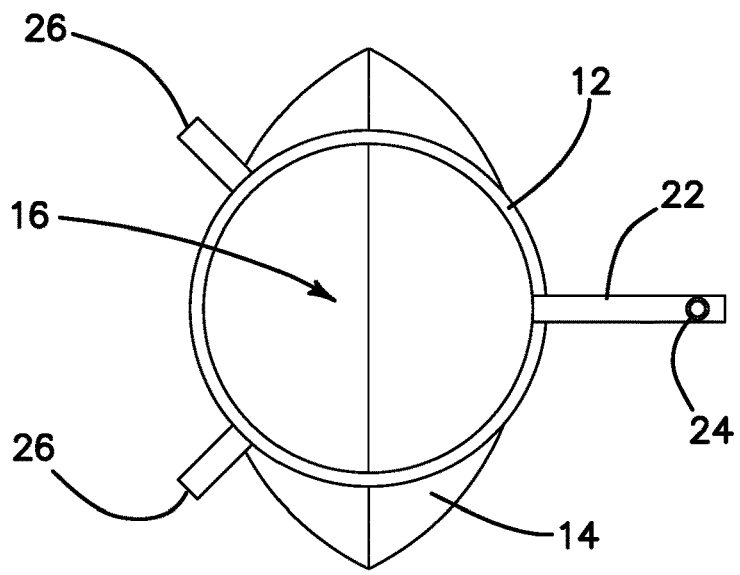
FIG. 2 is a top view of a containment bag in accordance with various embodiments of the present invention.
Figure 3:
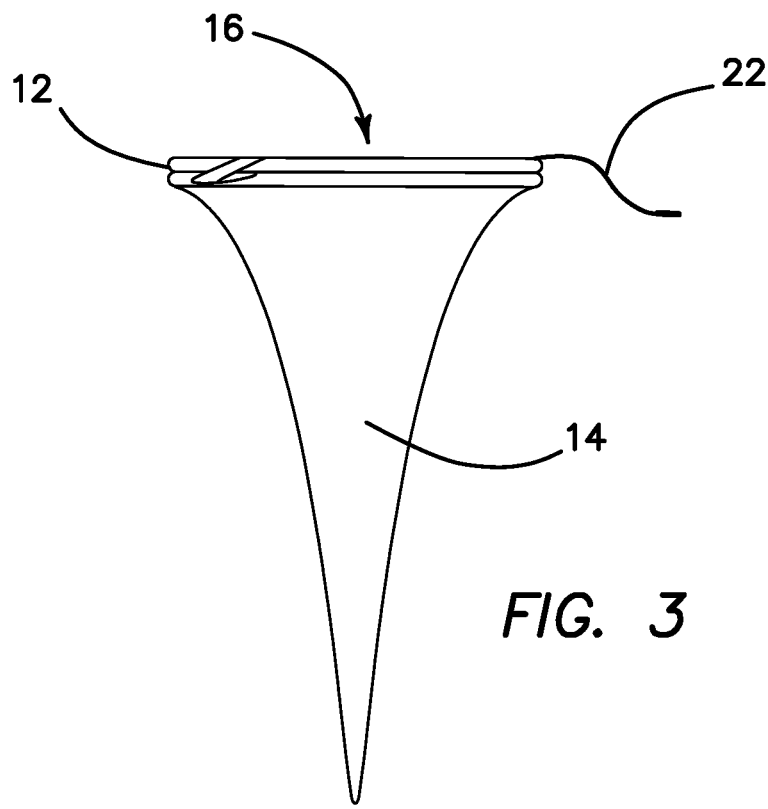
FIG. 3 is a side view of a containment bag in accordance with various embodiments of the present invention.
Figure 4:
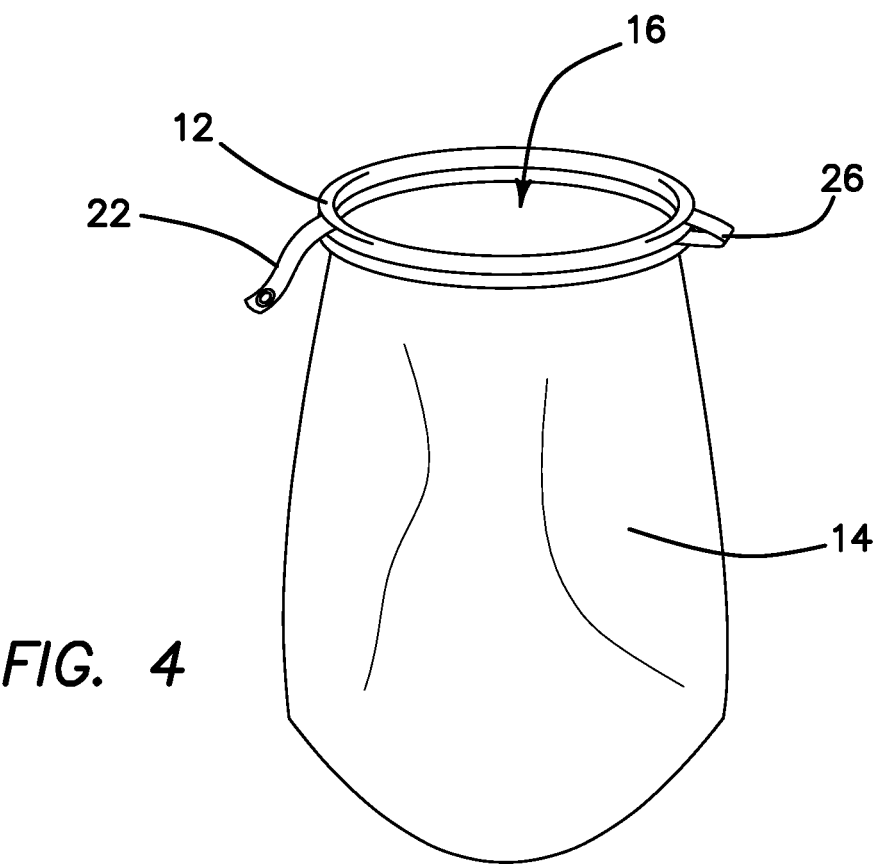
FIG. 4 is a side perspective view of a containment bag in accordance with various embodiments of the present invention.
Figure 5:
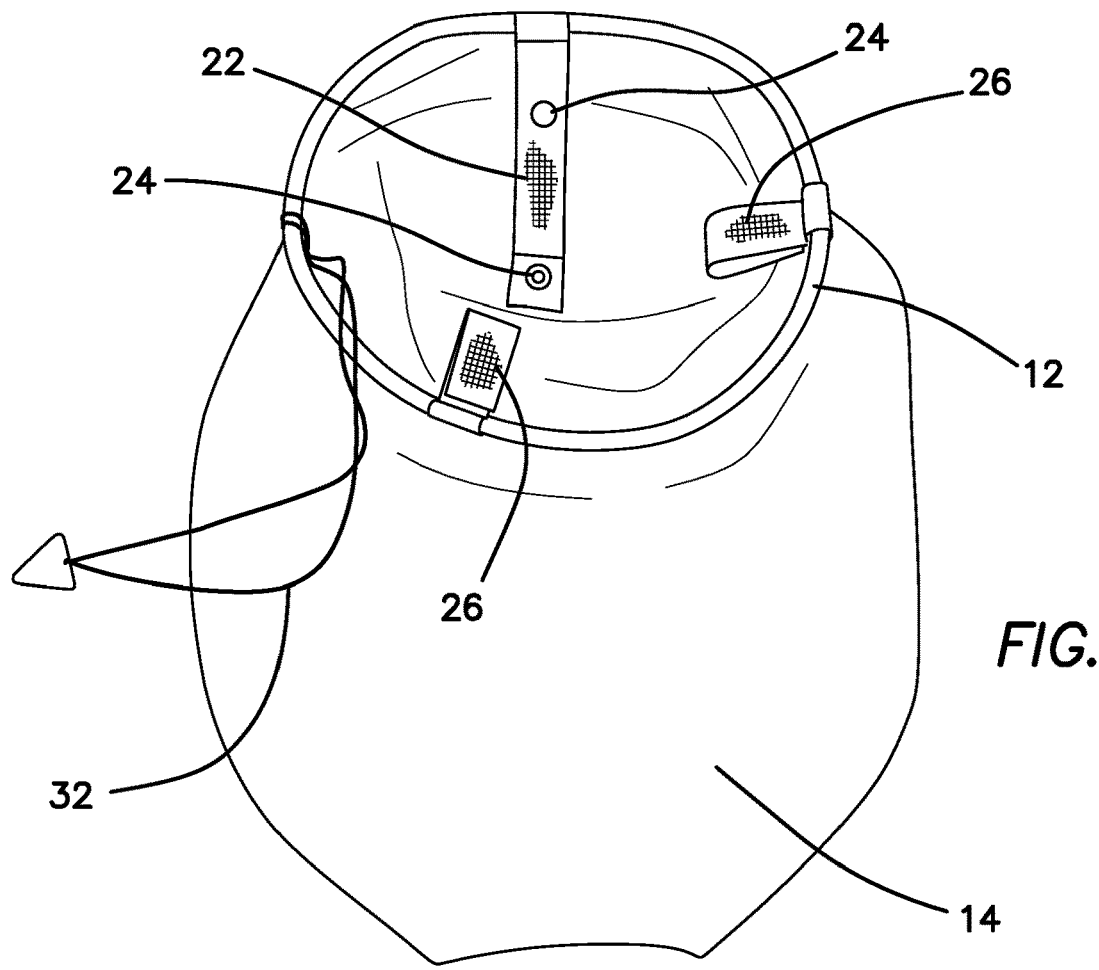
FIG. 5 is a top perspective view of a containment bag in accordance with various embodiments of the present invention.
Figure 6:
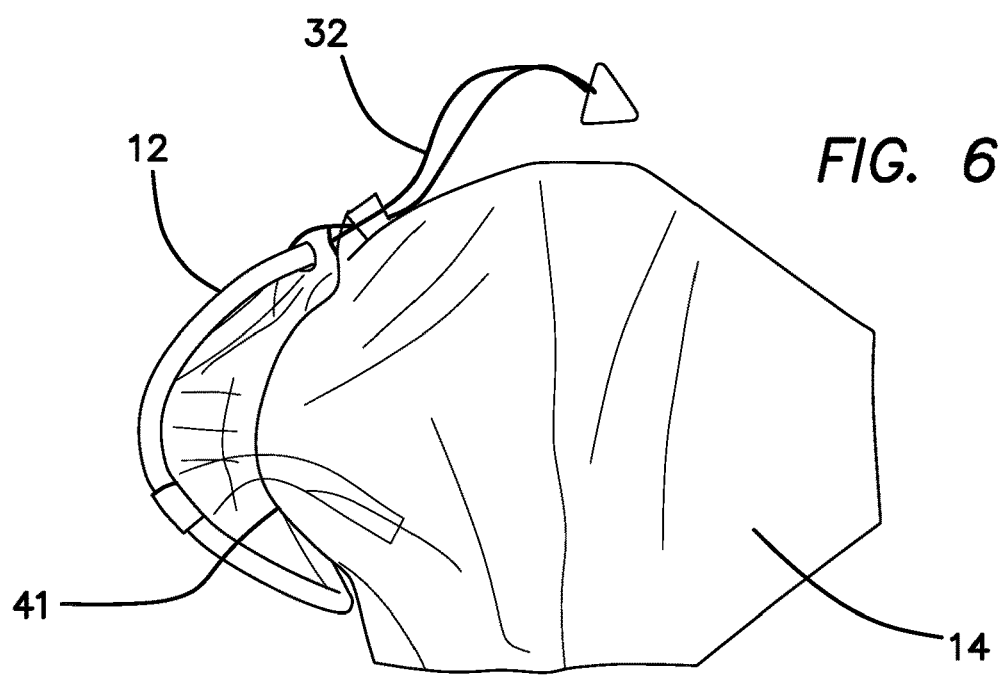
FIG. 6 is a bottom perspective view of a containment bag in accordance with various embodiments of the present invention.
Figure 7:
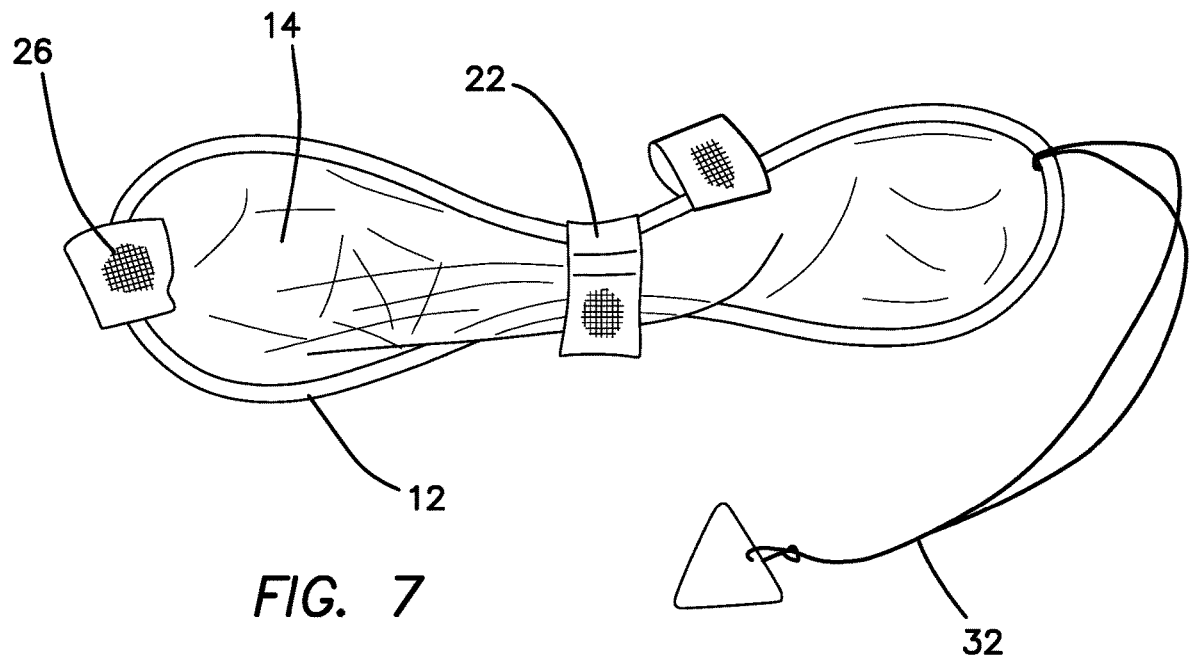
FIG. 7 is a top view of a containment bag in an insertion or compressed/confined state in accordance with various embodiments of the present invention.

Specimens retrieved during certain surgical, e.g., gynecological, procedures require specimen containment and extraction. In accordance with various embodiments, a specimen is placed in a containment bag prior to being reduced in size and extracted. In one such exemplary surgical operation, e.g., a laparoscopic hysterectomy, a specimen, e.g., a uterus, is dissected, mobilized and collected within the containment bag. The specimen is exteriorized to the surface of the body wall through a laparoscopic access port, trocar or through an incision in the body wall or opening in the patient. The incision size or length can range from 2.5 cm to 4 cm.

Placement of the containment bag and containment of a specimen inside the surgical space can be challenging especially involving large specimens, e.g., uteri greater than 20 weeks and/or 1,000 grams, and in some surgical procedures, such as laparoscopic hysterectomies. Limited space in the abdomen minimizes the space to place the containment bag. Single site gynecological procedures such as laparoscopic hysterectomies also have limited visualization of the surgical space and surroundings, especially in large uteri cases, as the volume of the specimen can occupy a vast majority of the surgical space. As such, full visualization of the specimen from the access site is not achieved in such cases, requiring the laparoscope to be constantly manipulated proximal to the access site to allow for visualization. The visualization of the surgical space may be further hindered by the addition of the containment bag, which can also occupy a large volume of the surgical space. Also, due to the limited surgical space, repositioning or generally moving of the bag relative to the specimen within the confined surgical space is also difficult. As such, the specimen size and containment bag size in a deployed state can limit visibility and a surgeon's working space.

Additionally, containment of a large specimen can require more manipulation of the bag in order to place the specimen in the bag. Furthermore, manipulation of the bag can be limited due to the bag itself and in particular its composition, size and/or shape. The film of the bag in one example provides a smooth yet durable surface and is arranged to minimize rough or abrasive surfaces to avoid potential tissue trauma or issues. However, such surfaces also minimize the ability to grasp and manipulate the containment bag. Moreover, the ring of the containment bag in various embodiments encloses the perimeter of the specimen before retrieval. As such, containment of the specimen includes a majority of the specimen volume occupying the containment bag. With the film encasing or otherwise covering the ring of the containment bag, the manipulation of the opening of the bag, e.g., up to the incision or body opening, is also difficult. Without friction on the film, slippage or unintended releasing of the bag may occur. As such, specimen placement, containment and retrieval can be dependent on the bag and the ease and ability to manipulate the containment bag.

In accordance with various embodiments and as shown for example in FIGS. 1-7, the containment bag 10 comprises a support or ring 12 and a film or a plurality of films 14 attached to the ring 12 to form an enclosed space or enclosure 16. In various embodiments, the support is a dual lumen ring and in other embodiments the support is shaped, sized and arranged to define or delimit the opening or proximal end of the containment bag. In various embodiments, the film is made of the same material as the ring and in one embodiment, the film is made of thermoplastic polyurethane. In various embodiments, the ring has a thickness or width greater than the thickness or width of the film. In various embodiments, the ring has an inner diameter and an outer diameter and the enclosure has a defined inner and outer diameter. In various embodiments, the enclosure's inner and outer diameters are greater than the inner and outer diameters of the ring. The film is therefore arranged to enclose a specimen inserted within an enclosure 16 defined or delimited by the film 14. In accordance with various embodiments, the enclosure defined by the film and/or ring has various shapes, dimensions, and is configured to capture and contain a particular specimen or a range of specimen sizes that is larger than a trocar incision size and/or to mitigate the potential spread or displacement of unwanted tissue. In various embodiments, the enclosure, defined by the film and/or ring, is arranged to have various shapes and/or dimensions to assist in the deployment, manipulation and/or removal of the containment bag within and/or out of the body cavity.

The support or ring 12 is compressible or deformable and, in various embodiments, compressible only in a direction traverse to a longitudinal axis of the containment bag. As such, the ring has an initial uncompressed state in which it delimits a pattern, e.g., circular, and a compressed state in which the ring delimits a narrowed or closed opening, e.g., an elongate oval or flatten hourglass pattern. In accordance with various embodiments, the film 14 is compressible and arranged to be rolled or gathered in a direction along or parallel to the longitudinal axis of the containment bag. In various embodiments, the containment bag is rolled, folded, gathered or fan-folded to collect, draw, bunch or compress the film, e.g., the length of the film, up to and/or within an inner periphery delimited by the ring and in various embodiments, when the ring is in a compressed state. The film of the containment bag in various embodiments has a rolled state where the film is rolled up to and/or against the ring and a deployed or unconfined state where the film is permitted to roll or extend away from the ring. Such states, configurations and operations are illustrated in FIGS. 8-12.

The containment bag further comprises one or more elongate strips, tabs or straps 22 arranged on or around the support or ring 12, the film 14 or any combination thereof. In various embodiments, the elongate straps are polyurethane film or polyester laminated fabric straps. In accordance with various embodiments, the film is confined or kept in its gathered or confined state by the one or more straps. In various embodiments, a strap is wrapped around a portion of the gathered film and the ring to retain the ring in its compressed state and the film in its confined state. Operationally, in one embodiment, a surgeon wraps the strap around the gathered film and the ring in its elongated shape for insertion into or through an incision or opening in a patient.

The containment bag further comprises one or more fasteners or connectors 24 attached to or integrated with the one or more straps 22. In various embodiments, the one or more fasteners are attached to the ring 12, film 14 or any combination thereof. The fastener or connector is attached to or integrated into one of the straps 22 and in various embodiments operationally secures the ring in its compressed state and the film in its confined state and as such, in various embodiments, places and/or maintains the containment bag in an insertion state. Once the bag is inserted into and placed in the body cavity of the patient, the fastener is released to allow the bag to expand into its deployed state. In various embodiments, the entire bag is arranged to be inserted and placed in its entirety within a patient's body. In various embodiments, the fastener is released or disengaged by using a grasper or a similar surgical or laparoscopic instrument to grab and pull against the strap having the fastener 24. In various embodiments, the fastener is snap type arrangement having a snap or connection portion disposed on one portion of the strap and a receiver portion disposed on another portion of the strap distal from the connection portion. In various embodiments, the fasteners arrangement is configured to remain covered by the strap or tab 22 and thus be unexposed to not interfere with insertions and manipulation of the bag.

In various embodiments, the containment bag includes or further comprises a pull cord or loop 32 and a tether tag 34. The pull cord and tether tag remain outside of the body while the remainder of the bag is entirely inserted into the body cavity. In accordance with various embodiments, the pull cord and tether tag provide outside user access, i.e., not within the body cavity, to manipulate the bag and assist in removal of the bag and any specimen with the bag from the patient.

In accordance with various embodiments, the containment bag further comprises one or more strips, projections, tabs or grips 26 arranged on or around the support or ring 12, the film 14 or any combination thereof. In various embodiments, the grips are polyurethane film or polyester laminated fabric grips. In accordance with various embodiments, the one or more grips provide anchors or grasping points to assist in the removal of the bag out of the patient's body. In various embodiments, the one or more grips or tabs 26 is formed as a loop and/or have textured or other surface features to provide grip access for a grasper or other similar surgical instruments to assist in the removal or manipulation of the containment bag. The grips are also configured to not interfere with the opening and/or the enclosure of the bag and any specimen contained therein. The grips are also provided in various embodiments to not snag or interfere with the removal, placement or manipulation of the bag and/or the specimen. Once the captured specimen is brought to the surface or outside the body along with a proximal portion of the containment bag, in various embodiments, the specimen may be extracted by grasping and pulling it out of the bag and/or by performing extracorporeal manual morcellation. In various embodiments, at least two grips or tabs are provided at about ninety degrees from each other and/or the one or more tabs to assist in providing a level and/or stable area to manipulate the bag from various angles or by using one or more instruments.

In accordance with various embodiments and illustrated for example in FIGS. 7-12, inserting the containment bag into the surgical space in a compressed/confined state does not impair visualization of the containment bag or other anatomical features. The elongated or narrowed shape created by securing the film of the bag via the strap and fastener arrangement facilitates the insertion of the bag through a small incision, placement into a surgical space and minimizes its obstruction of a surgeon's view or visualization.

In various embodiments, the user or surgeon is able to gather, roll, fold or fan-fold the film of the containment bag and secure it using the strap and fastener. The position of the strap and fastener allows the user to confine the film 14 as shown for example in FIG. 7. Once confined, the surgeon can introduce and place the containment bag via incision or access platform into a space that does not obstruct other anatomical features that require access. The confined bag can be deployed or released by undoing the fastener using for example a grasper to grasp and pull an excess or a portion of the tab or strap away from the fastener. Once released, the containment bag returns to its original or initial shape, state, or configuration.

In various embodiments, as specimen placement and containment are dependent on manipulation, having one or more tabs or grips 26 attached to the mouth or opening of the containment bag eases placement and containment of the specimen into and within the bag. In various embodiments, the positioning of the one or more grips, straps and/or cord loop eases control of the mouth or opening of the containment bag and/or to enclose the perimeter of the specimen, the bag or any combination thereof and/or allow the surgeon to control manipulation of the bag to facilitate specimen placement. In various embodiments, the one or more grips and/or straps are made from a laminated fabric providing additional friction properties to assist in the ability to grasp the grips and/or straps and control manipulation of the bag. Additionally, in accordance with various embodiments, an opening through or a loop formed on or by the grip and/or strap allow a surgeon to grab or insert a laparoscopic instrument there through to manipulate the bag.

Figure 19:
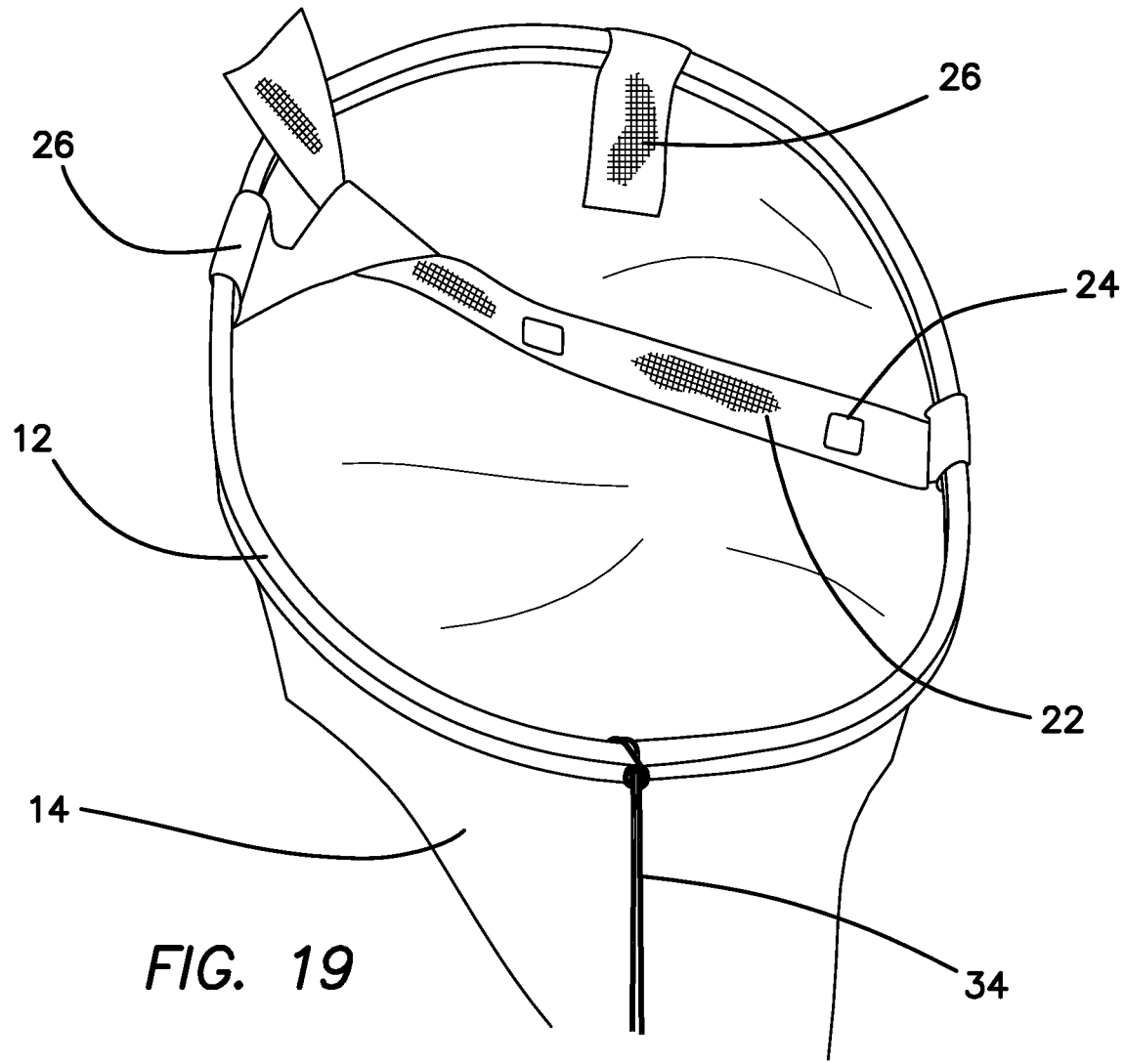
FIG. 19 is a top perspective view the strap of the containment bag threaded through a loop in a grip or tab in accordance with various embodiments of the present invention.

In various embodiments, the one or more elongate straps is operationally inserted into and through an opening, aperture or a formed loop of a grip or tab as shown for example in FIG. 19. As such, a connection is formed and thus aid in the containment and/or removal of the specimen and bag from the patient. In various embodiment, the connection assists in the removal for the bag to the surface of the abdomen in a parallel fashion with the aid of the cord loop outside of the abdomen also being moved distally or away from the patient or out of the patient cavity, thereby reducing or eliminating the possibility of the specimen or portions thereof from falling or spilling out from the bag if removal for example occurs at an extreme angle from the surgical or access site.

In accordance with various embodiments, the fastener and strap provides the ability for a quick engagement and disengagement of the containment bag. In various embodiments, straps and/or grips are provided across from each other and sized and/or shaped to allow them to be separately grasped and tied together. In various other embodiments, a pin or projection on one side of a strap is provided to be inserted into a key slot, hole, opening or aperture on the other side of the strap to be removably secured and thereby provide an engagement and release arrangement for the confinement and deployment of the containment bag.

In accordance with various embodiments, the strap and/or grip are made of a laminated fabric. In various embodiments, the strap and/or grip have specific texture and/or friction properties to facilitate and not interfere with the grasping or manipulation of the tab and/or grip within and outside the patient. In various embodiments, an inner periphery of the ring has a diameter and the strap has a length greater than the diameter of the inner periphery of the ring. In various embodiments, the strap has a length longer than a length of the grip or tab. In various embodiments, the tab defines or has a loop attached thereto in which the loop defines an opening through which the strap is threadable there through. In various embodiments, the loop of the tab is formed by the tab being connected to itself and in various embodiments with the strap threaded through the loop, the ring is in a partially compressed state in which the open end delimited by the ring is obstructed, no longer unobstructed in its initial uncompressed state, and less obstructed than the ring in the compressed state. In various embodiments, the loop of the tab has a diameter equal or greater than a width of the strap. In various embodiments, the strap has a width greater than a diameter of the loop of the tab. In various embodiments, the bag comprises of two/three tabs located in two/three different quadrants along the ring or support and the strap located at a third/fourth quadrant along the ring not occupied by any of the two/three tabs to facilitate support, deployment, securement and/or manipulation of the bag.

In accordance with various embodiments, the containment bag comprises a cinch 41. The cinch in various embodiments is a string, thread or cord disposed around the film between the open end and the closed end of the bag. Once the specimen is within the containment bag, the surgeon is able to close a top or proximal portion of the bag near the mouth or opening of the bag by drawing or pulling on the cinch. In various embodiments, the cinch is a dual cinch and by simultaneously pulling both ends of the cinch or cinch grasping regions in opposite directions using for example laparoscopic instruments or graspers, the surgeon can close a portion of the containment bag. The cinch in various embodiment can prevent a specimen or portions thereof from falling from the containment bag and can assist with the removal of the bag, as portions of the bag, e.g., at the mouth or opening of the bag, is in a closed or more confined state.

In various embodiments, one or more tabs or grips has a length of about 1.5 inches to 2.0 inches and in various embodiments is about 1.75 inches. The one or more straps have a length of about 4.25 inches to about 7.0 inches and in various embodiments is about 6.7 inches. The straps and/or grips have a thickness of about 0.018 inches to about 0.023 inches and in various embodiments is about 0.019 inches. In various embodiments, the at least one grip has a width of about 0.50 inches to 1.25 inches and in various embodiments is about 0.75 inches. The at least one strap has a width of about 0.50 inches to about 0.75 inches and in various embodiments is about 0.625 inches. As such, the strap and/or grip are arranged to facilitate the insertion, manipulation and removal of the containment bag and/or a specimen or portions thereof. In addition, in accordance with various embodiments, the size and/or shapes of straps and/or grips are configured to ensure or facilitate the manipulation, engagement and disengagement of the grips by a laparoscopic instrument. Furthermore, in accordance with various embodiments, the length of straps are configured to ensure or facilitate the capture or confinement of the film and ring in their confined/compressed state and the engagement and/or release of the fastener and/or tab to confine or release or deploy the bag.

In various embodiments, the distance from the bottom of the ring or support to the cinch and/or its cord's location is about 1.5 to 2.25 inches and in various embodiments about 1.5 inches. The location of the cinch in various embodiments ensures that the majority of the specimen volume is captured and not too high, e.g., less than 1.5 inches, that may make it more difficult for a surgeon to operate the cinch, as the ring or support can counteract the motion of closing the bag.

Figure 13:
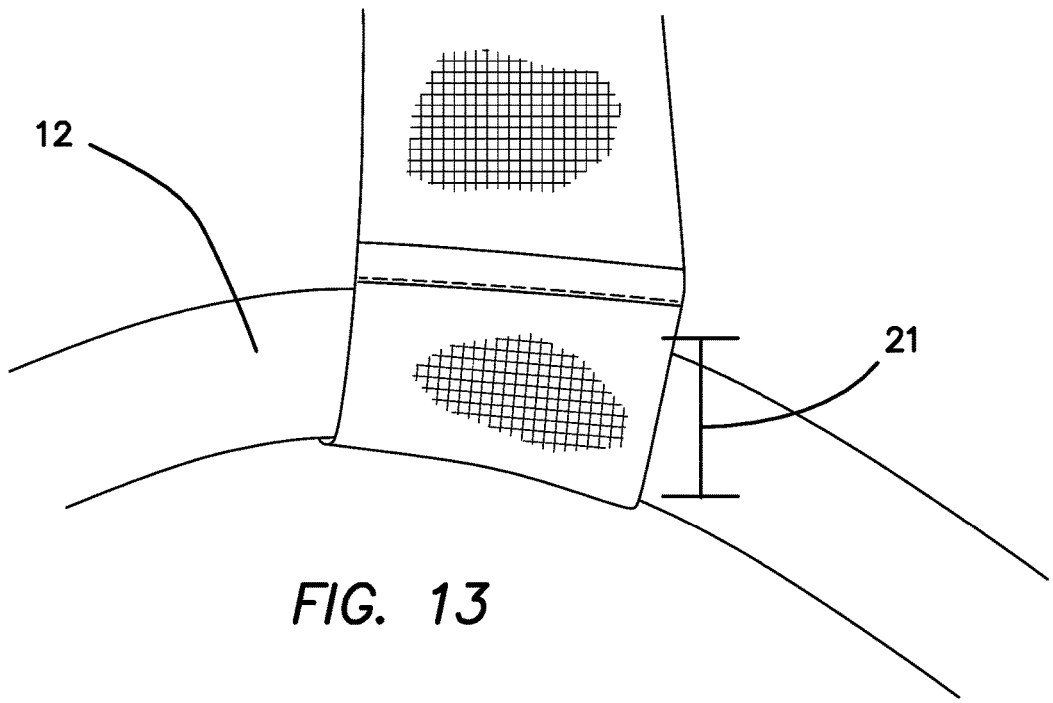
FIGS. 13-14 are perspective side views of the strap and/or grip and support or ring of the containment bag in accordance with various embodiments of the present invention.
Figure 8:
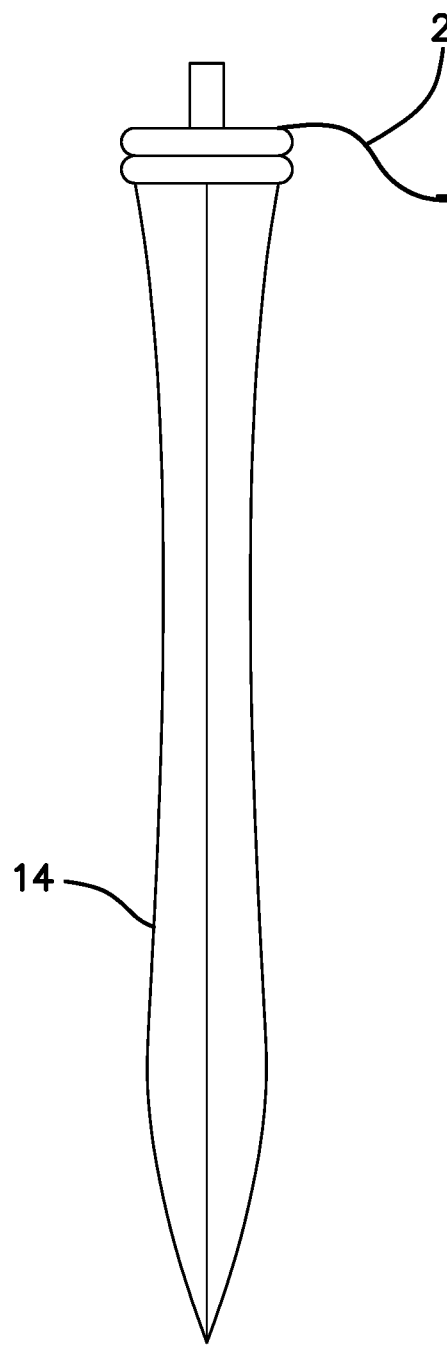
FIGS. 8-11 are side views of various embodiments of a containment bag in various states, positions or configurations in accordance with various embodiments of the present invention.
Figure 9:
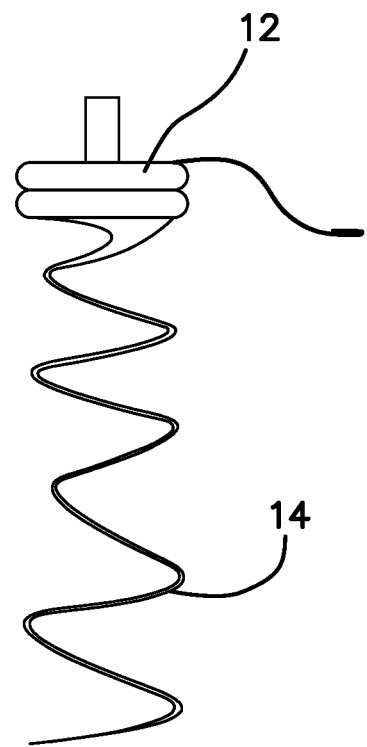
Figure 10:
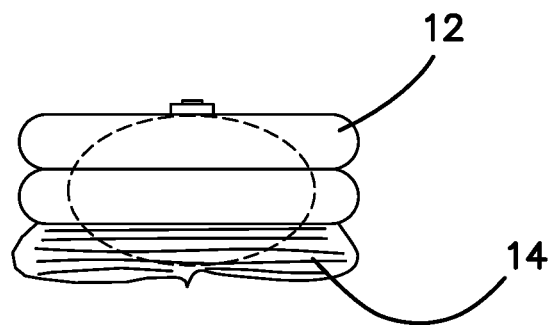
Figure 11:
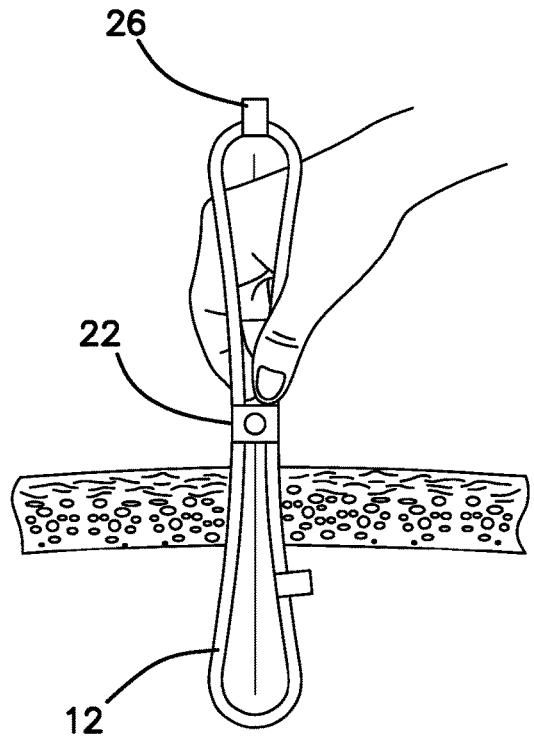
Figure 12:
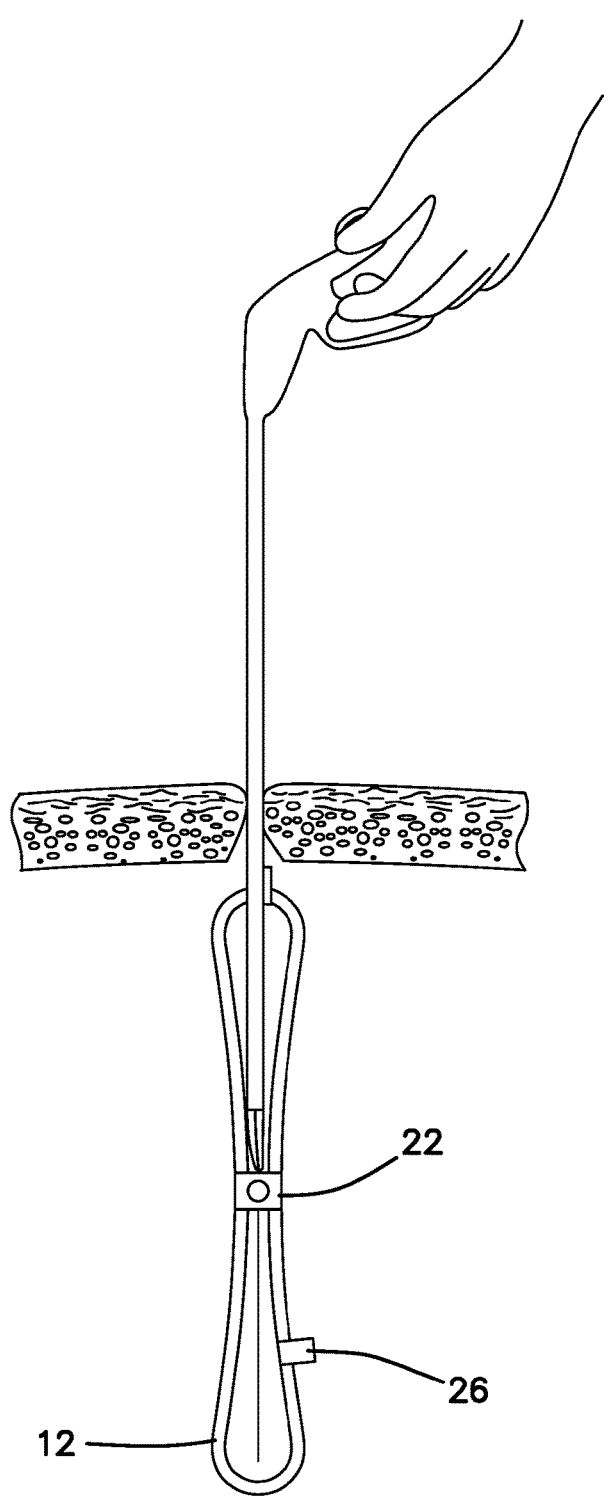
FIG. 12 is a side view of various embodiments of a containment bag in a compressed/confined position or state in conjunction with a surgical instrument or tool being inserted into a confined space through a covering or body wall in accordance with various embodiments of the present invention.
Figure 14:
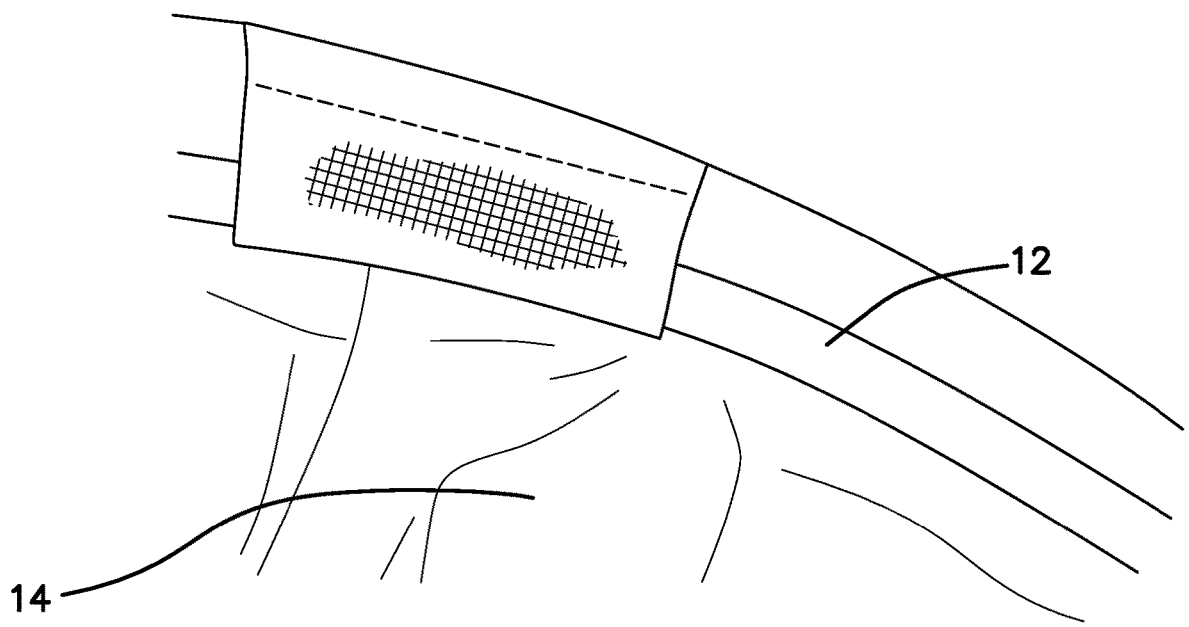

In accordance with various embodiments, one or more straps and/or grips are attached to the support 12 by one or more heat seals as illustrated in FIG. 13. The distance 21 between the heat seal is greater than the width and/or height of the support 12. In other embodiments, one or more seals or bonds on the strap and/or grips running along the top or one or more side edges of the support can be made to achieve fixation of the one or more straps and/or grips to the ring as illustrated in FIG. 14. As such, one end of the strap and/or grip forms a lumen through which a portion of the support is disposed there through. In various embodiments, the one or more straps and/or grips are bonded or adhered directly to the support. In accordance with various embodiments, the distance between the heat seal and/or the attachment of the strap to the support ensures that the straps remain in position on the support and yet does not interfere with its operation or the connection between the film and the support.

Figure 15:
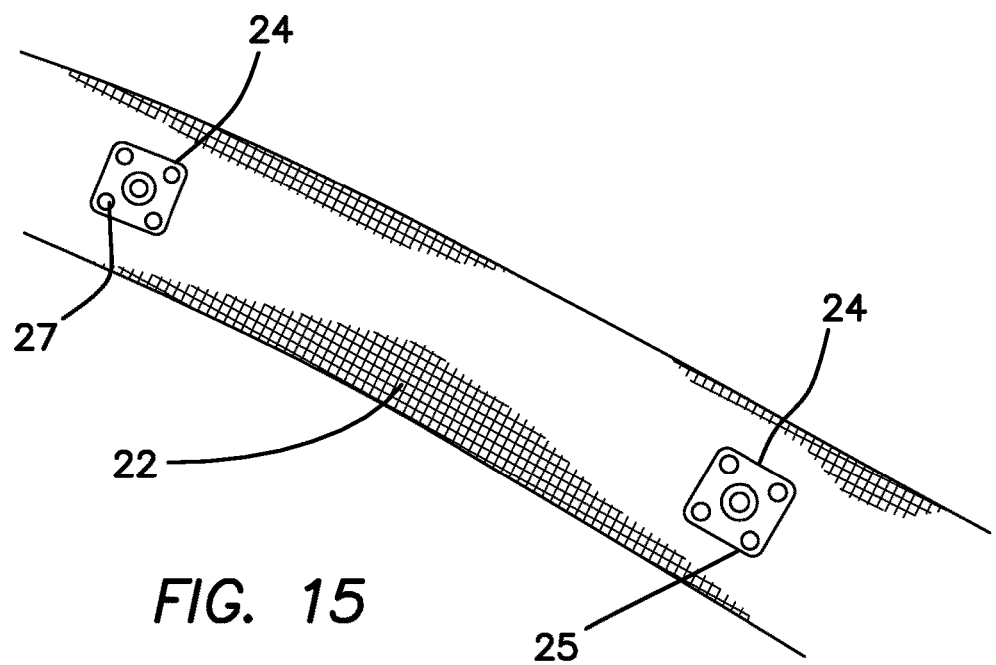
FIG. 15 is a top view of a strap and fastener attachment in accordance with various embodiments of the present invention.

In FIG. 15, in accordance with various embodiments, a strap 22 and fastener 24 is illustrated. As illustrated, the fastener 24 in one embodiment comprises an attachment portion 25 having one or more projections or pins extending from the tab to be removably connected to apertures or openings on a receiver portion 27 of the fastener. In various embodiments, the attachment portion and/or the receiver portion are integrated or adhered to the strap and in various embodiments, the positioning of each portion is reversed. In accordance with various embodiments, the projection and aperture connection is a friction fit. In various embodiments, the fastener is a hook and loop style arrangement. In various embodiments, the attachment portion and/or receiver portion is welded to the strap and in various embodiments, the attachment portion and/or receiver portion one or more boss pins piercing the strap and press fitted through holes or apertures of a respective attachment or receiver portion.

Figure 16:
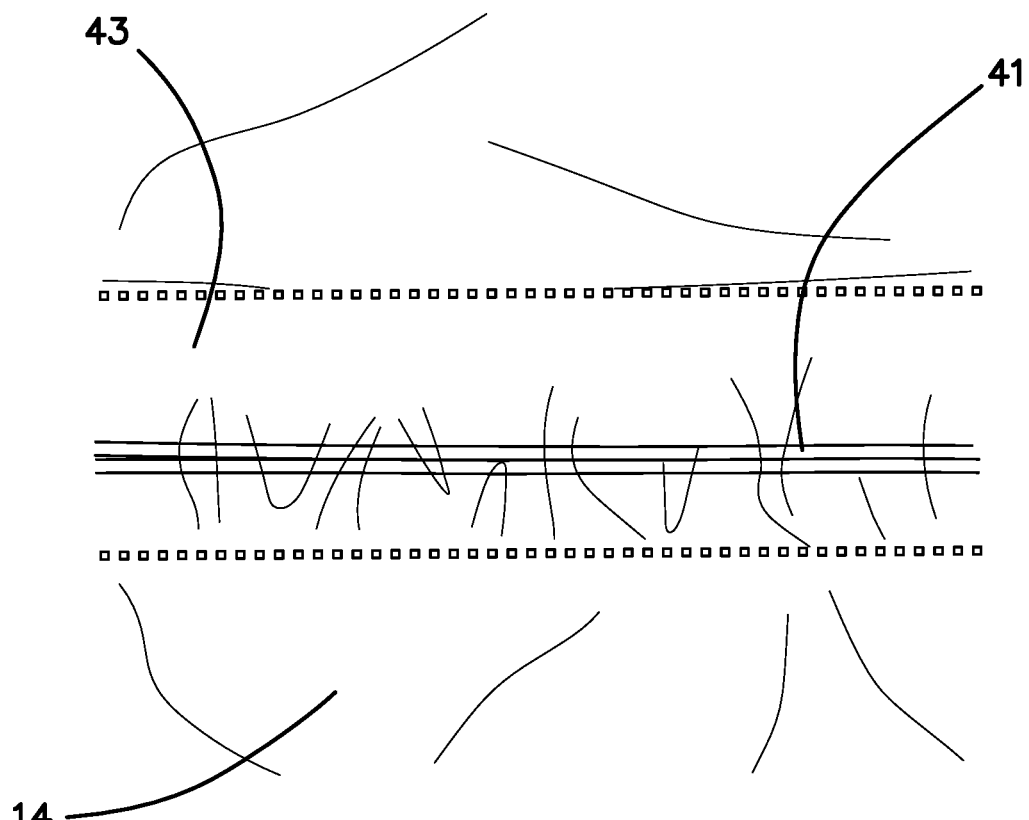
FIGS. 16-18 are side views of a cinch and film in accordance with various embodiments of the present invention.
Figure 17:
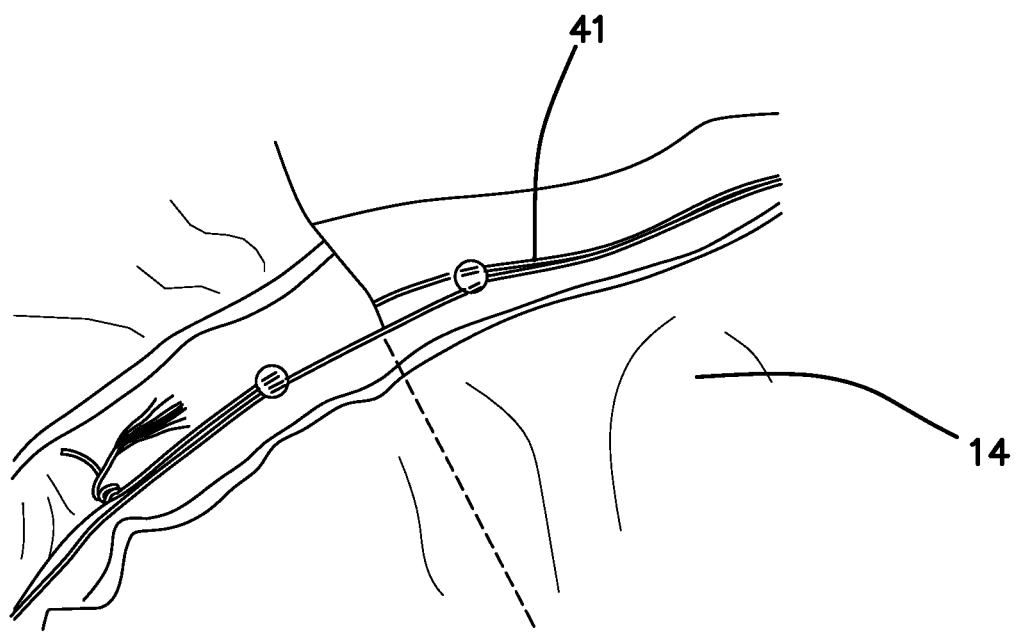
Figure 18:
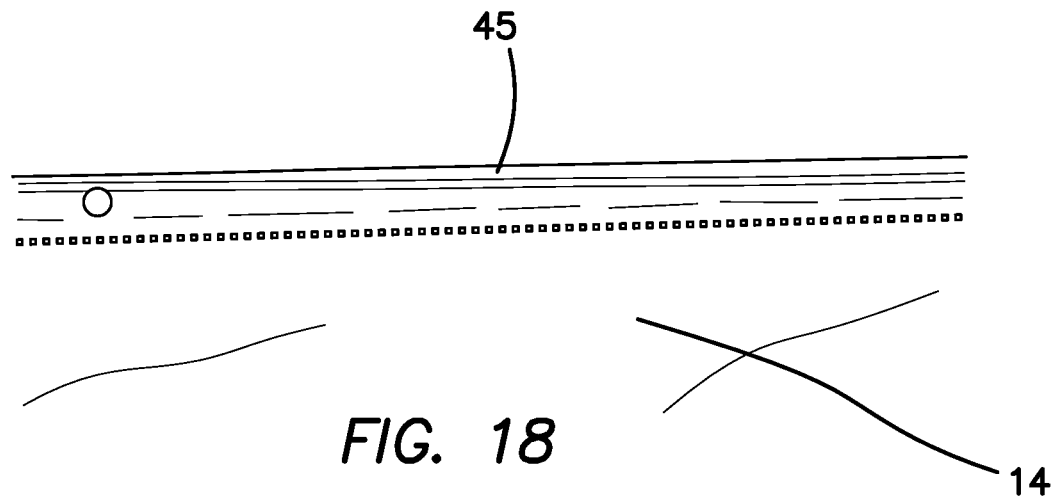

In reference to FIGS. 16-18, in various embodiments, the containment bag comprises a cinch 41. In various embodiments, one or more strips of film 43 are sealed to the film of the containment bag. In various embodiments, the film strips are made of the same material as the film of the containment bag. In various embodiments, the film strips have a length of about 7.5 inches and width of about 0.75 inches and are sealed at the top and bottom to the film of the containment bag to thereby enclose and capture portions of the cinch. In various embodiments, openings or thru holes are provided or made at one or both ends of the film strips and/or the film of the bag to allow the one or more cord loops to be fed in and through the film strips. In various embodiments, the cord loops are fixed, adhered or tied off on opposite ends, exposing only single cord loop per side. In various embodiments, one or more clips, tabs, or grips are attached to the cord to provide a larger area to grasp or access the cord of the cinch. In various embodiments, the film strips are provided to cover or keep the cinch unexposed to not interfere with any surrounding tissue or the insertion, removal or manipulation of the bag.

In various embodiments, as illustrated in FIG. 18, a sealed cord region 45 to enclose or capture the cord of the cinch is provided by folding the film of the bag onto itself and creating the cord region. After sealing off or forming the cord region, the excess or additional portion of the film is used to attach the ring with the opposite end of the film and is sealed in the same manner. Once the edges of the film of the bag are sealed, strands of cord or cord loop can be inserted and tied off or attached to form the cinch. In accordance with various embodiments, a cinch 41 may be formed by feeding a cord or cord loops through a plurality of openings or apertures in the film of the film or film strips of the bag and in other embodiments covered by an additional film or film strip to cover or keep the cinch unexposed to not interfere with any surrounding tissue or the insertion, removal or manipulation of the bag.

In various embodiments, the cinch is a dual cinch with one end disposed outside the film and another end disposed on an opposing side outside the film in which movement of the ends of the dual cinch away from the bag in opposing directions constricts the film, closing a pathway from the closed end of the bag to the open end of the bag. In various embodiments, the cinch is disposed within film strips attached and heat sealed to the film and/or the film strips having opening through which one or more ends of the cinch extends there through.

In various embodiments, the support or ring can be oval or non-circular and defining an open end or opening having a similar shape. In various embodiments, the support or ring has a thickness greater than a thickness of the film and in various embodiments, the ring is deformable only in a direction traverse to a longitudinal axis of the bag. In various embodiments, the ring or support has a predefined resiliency or spring rate to spring back from the compressed state to an initial uncompressed state. In various embodiments, the ring in the initial uncompressed state defines a circular opening and the ring in the compressed state defines a narrowed opening.

In various embodiments, the film connected to the ring covers an entire periphery of the ring. In various embodiments, the film is a monolithic film sheet being impermeable and having no apertures or openings there through. In various embodiments, the film has pre-formed creases to induce folding of the film into an insertion configuration. In various embodiments, the film comprises a plurality of films connected to each other and to the ring to form sidewalls and a closed end and defining the interior of the enclosure. In various embodiments, the film is folded over itself with a pair of first side edges being attached to each other and a pair of second side edges being attached to each other to form side walls and a closed end and defining the interior of the enclosure. In various embodiments, the enclosure of the bag has an inner diameter defined by the inner periphery of the ring and/or the enclosure has an outer diameter greater than an outer diameter of the ring defined by an outer periphery of the ring. In various embodiments, the film is in contact with the ring and the ring is not able to roll the film around the ring and/or the film is gatherable in a direction along a longitudinal axis of the tissue containment bag. In various embodiments, the film, in the confined state, is gathered up to and within an outer periphery of the ring. In various embodiments, the film, in a deployed state, is extended away from and outside an outer periphery of the ring. In various embodiments, the enclosure has a minimum fillable volume with the film being in the confined state and a maximum fillable volume with the film being in the deployed state.

In accordance with various operational aspects of the tissue containment bag, the bag may be prepared for deployment, deployed in a confined space, such as patient's body cavity or a surgical simulator or trainer, and/or utilized to remove a specimen, simulated or not, from the confined space. As such, in accordance with various embodiments, the ring or support in a compressed state and the film in a confined state can be placed, secured and inserted into the confined space with the ring in a compressed state and the film in a confined state. In various embodiments, the film is released from its confined state to its deployed state and the ring from its compressed state to its uncompressed state and/or a specimen can be placed through an opening defined by the ring in its uncompressed state and into the enclosure defined by the film in its deployed state. In various embodiments, the opening or open end defined by the ring can be partially closed and/or the ring secured in a partially compressed state while the film remains in its deployed state. In various embodiments, the ring is removed in its partially compressed state out of the confined space with the film remaining within the confined space, releasing the ring from its partially compressed state to move to its uncompressed state. The specimen can be removed from the enclosure and out through the opening of the ring. In various embodiments, the enclosure between the ring or support and the film can be closed and/or closed by pulling a cinch way from the film. In various embodiments, a surgical instrument or tool can be utilized to insert, interact and/or manipulate the bag and portions thereof and such a tool or device may be a grasper or the like and/or a specific set of tools or instruments to separately perform some or all of these actions may be provided.

Examples of bags and related accessories and their operational use are described in U.S. patent application Ser. Nos. 14/885,072; 15/068,366; and Ser. No. 15/498,157, the entire disclosures of which are hereby incorporated by reference as if set in full herein. The above description is provided to enable any person skilled in the art to make and use the tissue containment devices or systems and perform the methods described herein and sets forth the best modes contemplated by the inventors of carrying out their inventions. Various modifications, however, will remain apparent to those skilled in the art. It is contemplated that these modifications are within the scope of the present disclosure. Different embodiments or aspects of such embodiments may be shown in various figures and described throughout the specification. However, it should be noted that although shown or described separately each embodiment and aspects thereof may be combined with one or more of the other embodiments and aspects thereof unless expressly stated otherwise. It is merely for easing readability of the specification that each combination is not expressly set forth.

Although the present invention has been described in certain specific aspects, many additional modifications and variations would be apparent to those skilled in the art. It is therefore to be understood that the present invention may be practiced otherwise than specifically described, including various changes in the size, shape and materials, without departing from the scope and spirit of the present invention. Thus, embodiments of the present invention should be considered in all respects as illustrative and not restrictive.

The invention claimed is:

1. A tissue containment bag comprising:
  a ring having an inner periphery delimiting an open end, the ring being deformable from an uncompressed state in which the open end delimited by the ring is unobstructed to a compressed state in which the open end delimited by the ring is partially obstructed;
  a film connected to the ring to form an enclosure having an interior and a closed end, the interior of the enclosure being accessible through the open end delimited by the ring, the film and the interior of the enclosure being extendable to a deployed state in which a distal-most end of the film extends away from the ring from a confined state in which the film including the distal-most end is confined to a position adjacent to ring; and
  a strap connected and encircling the ring and a portion of the film, with the strap being textured relative to a smooth outer surface of the film, the strap having a fastened state in which the strap in the fastened state secures the ring in the compressed state and, simultaneously, the film in the confined state and the strap has an unfastened state in which the strap, simultaneously, releases the ring from its compressed state and the film from its confined state.

2. The tissue containment bag of claim 1 wherein the strap is heat-sealed to itself connecting the strap to the ring and the film; and the film is heat-sealed to the ring and the ring is not able to roll the film around the ring.

3. The tissue containment bag of claim 1 wherein the strap comprises a fastener attachment to releasably attach the strap from the fastened state to the unfastened state.

4. The tissue containment bag of claim 3 wherein the inner periphery of the ring has a diameter and the strap has a length greater than the diameter of the inner periphery of the ring.

5. The tissue containment bag of claim 4 wherein the strap has an outer surface and an inner surface and the fastener attachment comprises a connector and a receiver disposed on the inner surface of the strap, the connector being disposed near a first end of the strap and the receiver being disposed near a second end of the strap.

6. The tissue containment bag of claim 5 wherein the first end of the strap is connected to the ring and the second end of the strap is not connected to the ring.

7. The tissue containment bag of claim 6 wherein the second end of the strap is connected to the ring and the first end of the strap is not connected to the ring.

8. The tissue containment bag of claim 6 further comprising a tab connected to the ring at a position opposite of the strap, the strap having a length longer than a length of the tab.

9. The tissue containment bag of claim 8 wherein the tab has a loop defining an opening through which the strap is threadable there through.

10. The tissue containment bag of claim 9 wherein, with the strap threaded through the loop, the ring is in a partially compressed state in which the open end delimited by the ring is obstructed, no longer unobstructed in its initial uncompressed state, and less obstructed than the ring in the compressed state.

11. The tissue containment bag of claim 10 wherein the loop of the tab has a diameter equal or greater than a width of the strap.

12. The tissue containment bag of claim 10 wherein the strap has a width greater than a diameter of the loop of the tab.

13. The tissue containment bag of claim 12 wherein the tab extends away from the ring and the strap extends away from the ring and the tab, the tab and strap being made of the same material.

14. The tissue containment bag of claim 10 further comprising a cord attached to the ring, the strap having a length shorter than a length of the cord.

15. The tissue containment bag of claim 14 further comprising a cinch attached to the film and disposed between the ring and the closed end, in which movement of the cinch away from the bag constricts the film, closing a pathway from the closed end of the film to the open end of the ring.

16. The tissue containment bag of claim 15 wherein the cinch is disposed within film strips attached and heat sealed to the film and the film strips has one or more openings through which one or more ends of the cinch extends there through.

17. The tissue containment bag of claim 14 further comprising a cinch attached to the film and disposed between the ring and the closed end; wherein the cinch is a dual cinch with one end disposed outside the film and another end disposed on an opposing side outside the film in which movement of the ends of the dual cinch away from the bag in opposing directions constricts the film, closing a pathway from the closed end of the film to the open end of the ring.

18. A method of removing a specimen with a tissue containment bag, the method comprising:
  providing a tissue containment bag comprising a ring and a film connected to the ring, the film defining an enclosure;
  placing the ring in a compressed state and the film in a confined state;
  securing the ring in its compressed state and the film in its confined state;

inserting the tissue containment bag into a patient's cavity with the ring in a compressed state and the film in a confined state;

releasing the film from its confined state to its deployed state and the ring from its compressed state to its uncompressed state;

placing a specimen through an opening defined by the ring in its uncompressed state and into the enclosure defined by the film in its deployed state;

partially closing the opening defined by the ring to secure the ring in a partially compressed state while the film remains in its deployed state;

removing the ring in its partially compressed state out of the patient's cavity with the film remaining within the patient's cavity;

releasing the ring from its partially compressed state to move to its uncompressed state; and removing the specimen from the enclosure and out through the opening of the ring;

wherein the securing the ring in its compressed state and the film in its confined state further comprises wrapping a strap connected to the ring around portions of the ring and portions of the film and fastening the strap to itself and the releasing the film from its confined state to its deployed state and the ring from its compressed state to its uncompressed state further comprises unfastening the strap from itself.

19. The method of claim 18 wherein the partially closing the opening defined by the ring to secure the ring in a partially compressed state while the film remains in its deployed state further comprises threading the strap through a loop defined by a tab connected to the ring and pulling the strap through the loop to narrow the opening defined by the ring.

* * * * *